United States Patent [19]

Soos et al.

[11] Patent Number: 5,906,816

[45] Date of Patent: *May 25, 1999

[54] METHOD FOR TREATMENT OF AUTOIMMUNE DISEASES

[75] Inventors: Jeanne M. Soos; Joel Schiffenbauer; Howard Marcellus Johnson, all of Gainesville, Fla.

[73] Assignee: University of Florida, Gainesville, Fla.

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/406,190

[22] Filed: Mar. 16, 1995

[51] Int. Cl.$^6$ .................................................. A01N 25/00
[52] U.S. Cl. .......................... 424/85.4; 424/85.6; 512/21; 530/351
[58] Field of Search ................................ 424/85.4, 85.6; 514/21; 530/351

[56] References Cited

U.S. PATENT DOCUMENTS

| | | |
|---|---|---|
| 4,997,646 | 3/1991 | Hansen et al. . |
| 5,109,382 | 4/1992 | Cummins, Jr. . |
| 5,372,808 | 12/1994 | Blatt et al. . |

FOREIGN PATENT DOCUMENTS

| | | |
|---|---|---|
| WO 90/90806 | 9/1990 | WIPO . |
| WO 94/10313 | 5/1994 | WIPO . |
| WO 95/27499 | 10/1995 | WIPO . |
| WO 95/27502 | 10/1995 | WIPO . |

OTHER PUBLICATIONS

Bazer, Medline AB #92075131, (1991).
Pontzel, Biosis AB #91:526987, (1991).
Sierra et al., "Multiple Sclerosis", Secretion of IL–2, IFN–τ+PGE$_2$ +Effect, Neurologia (1992), 7/9 pp. 247–253.
Arnason, B.G.W., and Reder, A.T., "Interferons and Multiple Sclerosis," *Clin. Neuropharmacol.* 17(6):495–547 (1994).
Brod, S.A., and Burns, D.K., "Suppression of Relapsing Experimental Autoimmune Encephalomyelitis in the SJL/J Mouse by Oral Administration of Type I Interferons," *Neurology* 44:1144–1148 (1994).
Bazer, F.W., and Johnson, H.M., "Type I Conceptus Interferons: Maternal Recognition of Pregnancy Signals and Potential Therapeutic Agents," *Am. J. Reproduc. Immunol.* 26:19–22 (1991).
Brod, S.A., et al., "Modification of Acute Experimental Autoimmune Encephalomyelitis in the Lewis Rat by Oral Administration of Type 1 Interferons," *J. Interfer. & Cytokine Res.* 15:115–122 (1995).
Duquette, P., et al., [IFNB Multiple Sclerosis Study Group], "Interferon Beta–1b is Effective in Relapsing–Remitting Multiple Sclerosis, I. Clinical Results of a Multicenter, Randomized, Double–Blind Placebo–Controlled Trial," *Neurology* 43:655–661 (1993).
Pontzer, C.H., et al., "Antiproliferative Activity of a Pregnancy Recognition Hormone, Ovine Trophoblast Protein–1," *Cancer Res.* 51:5304–5307 (1991).
Soos, J.M., et al., "The Novel Type I Interferon Tau Development and Superantigen Reactivation of Experimental Allergic Encephalomyelitis in Mice without Associated Toxicity," *Faseb J. of Exper. Biol.* 9(4):A1025 (1995).
Soos, J.M., and Johnson, H.M., "Type I Interferon Inhibition of Superantigen Stimulation: Implications for Treatment of Superantigen–Associated Disease," *J. Interferon and Cytokine Res.* 15:39–45 (1995).

*Primary Examiner*—Cecilia J. Tsang
*Assistant Examiner*—Patrick R. Delaney
*Attorney, Agent, or Firm*—Joanne R. Petithory; Charles K. Sholtz; Peter J. Dehlinger

[57] ABSTRACT

Methods of treating autoimmune disorders, such as multiple sclerosis, are disclosed. The methods employ administration of interferon-tau (IFNτ) in a therapeutically-effective dose.

11 Claims, 4 Drawing Sheets

METHOD FOR TREATMENT OF AUTOIMMUNE DISEASES

This work was supported in part by Grants Nos. AI 25904, CA 38779 and HD 26006 from the National Institutes of Health. Accordingly, the United States Government has certain rights in this invention.

FIELD OF THE INVENTION

The present invention relates to the use of IFNτ as a treatment for conditions relating to immune system hypersensitivity. More particularly, the present invention relates to the treatment of autoimmune diseases, including multiple sclerosis, rheumatoid arthritis, lupus erythematosus and type I diabetes mellitus.

REFERENCES

Ausubel, F. M., et al., in *CURRENT PROTOCOLS IN MOLECULAR BIOLOGY* (John Wiley & Sons, Inc., Media, Pa.).

Bartol, F. F., et al., *Biol. Reprod.* 32:681–693 (1985).

Bazer, F. W., et al., *Biol. Reproduc.* (abstract only) 40(suppl):63 (1989).

Bazer, F. W., et al., PCT publication WO/94/10313, published May 11, 1994.

Bazer, F. W., and Johnson, H. M., *Am. J. Reprod. Immunol.* 26:19–22 (1991).

Beames, et al., *Biotechniques* 11:378 (1991).

Bergdoll, M. S., et al., *Lancet* 1:1071–1072 (1981).

Brocke, S., et al., *Nature* 365:642–644 (1993).

Carlsson, R., and Sjogren, H. O., *Cell Immunol.* 96:175–183 (1985).

Carlsson, R., et al., *J. Immunol.* 140:2484–2488 (1988).

Charlier, M., et al., *Mol. Cell Endocrinol.* 76:161–171 (1991).

Clayman, C. B., Ed., *AMERICAN MEDICAL ASSOCIATION ENCYCLOPEDIA OF MEDICINE* (Random House, New York, N.Y.), 1991.

Cross, J. C., and Roberts, R. M., *Proc. Natl. Acad. Sci. USA* 88:3817–3821 (1991).

Day, M. J., et al., *Clin. Immunol. Immunopathol.* 35(1):85–91 (1985).

Degre, M., *Int. J. Cancer* 14:699–703 (1974).

Dianzani, F., *J. Interferon Res., Special Issue* 5(92):109 (1992).

Fent, K., and Zbinden, G., *Trends Pharm. Sci.* 8:100–105 (1987).

Figuero, F., et al., *Immunogenetics* 15:(4):399–404 (1982).

Finter, N. B., et al., *Drugs* 42(5):749 (1991).

Fleischer, B., and Schrezenmeier, H., *J. Exp. Med.* 176:1697–1707 (1988).

Francis, M. L., et al., *AIDS Res. and Human Retroviruses* 8(2):199 (1992).

Fritz, R. B., et al., *J. Immunol.* 130(3):1024–1026 (1983).

Gnatek, G. G., et al., *Biol. Reprod.* 41:655–664 (1989).

Godkin, J. D., et al., *J. Reprod. Fertil.* 65:141–150 (1982).

Godkin, J. D., et al., *J. Reprod. Fertil.* 71:57–64 (1984).

Helmer, S. D., et al., *J. Reprod. Fert.* 79:83–91 (1987).

Herman, A., et al., *Ann. Rev. Immunol.* 9:745–772 (1991).

IFNβ Multiple Sclerosis Study Group, *Neurology* 43(4):655 (1993).

Ihle, J. N., et al., *Trends Biol. Sci.* 19:222–227 (1994).

Imakawa, K., et al., *Nature* 330:377–379 (1987).

Imakawa, K., et al., *Mol. Endocrinol.* 3:127 (1989).

Janeway, C. A., et al., *Immunol. Rev.* 107:61–88 (1989).

Jarpe, M. A., et al., *Protein Engineering* 7:863–867 (1994).

Johnson, H. M., and Magazine, H. I., *Int. Arch. Allergy Appl. Immunol.* 87:87–90 (1988).

Johnson, H. M., et al., *FASEB J.* 5:2706–2712 (1991).

Johnson, H. M., et al., *Sci. Am.* 270(5):40–47 (1994).

Kalman, B., et al., *J. Neuroimmunol.* 45:83–88 (1993).

Kaplan, J. M., et al., *Int. J. Immunopharmacol.* 15(2):113–123 (1993).

Kemppainen, R. J., and Clark, T. P., *Vet. Clin. N. Am. Small Anim. Pract.* 24(3):467–476 (1994).

Kim, C., et al., *J. Exp. Med.* 174:1431 (1991).

Klein, J., et al., *Immunogenetics* 17:553 (1983).

Klemann, S. W., et al., *Nuc. Acids Res.* 18:6724 (1990).

Kotzin, B. L., et al., *J. Exp. Med.* 265:1237 (1987).

Kristensen, A. T., et al., *J. Vet. Intern. Med.* 8(1):36–39 (1994).

Langford, M. P., et al., *Infect. Immun.* 22:62–68 (1978).

Leaman, D. W., et al., *J. INF Res.* 12:1–11 (1992).

Maniatis, T., et al., in *MOLECULAR CLONING: A LABORATORY MANUEL*, Cold Spring Harbor Laboratory (1982).

Martal, J., et al., *J. Reprod. Fertil.* 56:63–73 (1979).

Martin, E. W., in *DISPENSING OF MEDICATION: A PRACTICAL MANUAL ON THE FORMULATION AND DISPENSING OF PHARMACEUTICAL PRODUCTS* (Mack Publishing Co., Easton, Pa.), 1976.

Mirando, M. A., et al., *Biol. Reprod.* 43:1070–1078 (1990).

Mirando, M. A., et al., *J. Reprod. Fertil.* 93:599 (1991).

Ott, T. L., et al., *J. INF Res.* 11:357–364 (1991)

Panitch, H. S., et al., *Neurology* 37:1097–1102 (1987a).

Panitch, H. S., et al., *Lancet* i:893–895 (1987b).

Panitch, H. S., and Bever, C. T., Jr., *J. Neuroimmunol.* 46:155–164 (1993).

Pontzer, C. H., et al., *Cancer Res.* 51:5304–5307 (1991).

Powell, M. B., et al., *Int. Immunol.* 2(6):539–544 (1990).

Reilly, P. R., et al., *BACULOVIRUS EXPRESSION VECTORS: A LABORATORY MANUAL*, 1992.

Roberts, R. M., et al., *Endocrin. Rev.* 13:432–452 (1992).

Rott, O., et al., *Int. Immunol.* 4:347–353 (1992).

Schiffenbauer, J., et al., *Proc. Natl. Acad. Sci. USA* 90:8543–8546 (1993).

Selmaj, K. W., and Raine, C. S., *Ann. Neurol.* 23:339–346 (1988).

Singer, P. A., et al., *Proc. Natl. Acad. Sci. USA* 83:7018–7022 (1986).

Skopets, B., et al., *Vet. Immunol. Immunopathol.* 34:81–96 (1992).

Smith, P. K., et al., *Anal. Biochem.* 150:76 (1985).

Soos, J. M., et al., *J. Neuroimmunol.* 43:39–44 (1993).

Soos, J. M., and Johnson, H. M., *J. Interferon Res.* 15:39–45 (1995).

Stewart, H. J., et al., *J. Mol. Endocrinol.* 2:65 (1989).

Vallet, J. L., et al., *Biol. Reprod.* 37:1307 (1987).

Weinstock-Guttman, B., et al., *Ann. Neurol.* 37:7–15 (1995).

Werner, L. L., et al., *Vet. Immunol. Immunopathol.* 8(1–2):183–192 (1985).

Whaley, A. E., et al., *J. Biol. Chem.* 269(14):10864–10868 (1994).

Wraith, D. C., et al., *Cell* 59:247 (1989).

White, J., et al., *Cell* 56:27–35 (1989).

Zamvil, S. S., et al., *Ann. Rev. Immunol.* 8:579–621 (1990).

Zamvil, S. S., and Steinman, L., *Ann. Rev. Immunol.* 8:579–621 (1990).

BACKGROUND OF THE INVENTION

The immune system is the body's primary defense against diseases caused by invading organisms, such as bacteria, viruses or parasites, as well as diseases caused by abnormal growth of the body's own tissues (i.e., cancerous tumors). Normally, the immune system is able to distinguish the body's normal tissues, or self, from foreign or cancerous tissue, or non-self. The loss of recognition of a particular tissue as self, and the subsequent immune response directed against that tissue, typically results in an "autoimmune response" that often has serious clinical consequences.

One specific example of such an autoimmune disease is multiple sclerosis (MS), a progressive disease of the central nervous system (CNS) in which patches of myelin (the protective covering of nerve fibers) in the brain and spinal cord are destroyed by the body's own immune system. This destruction leads to scarring and damage to the underlying nerve fibers, and may manifest itself in a variety of symptoms, depending on the parts of the brain and spinal cord that are affected. Spinal cord damage may result in tingling or numbness, as well as a heavy and/or weak feeling in the extremities. Damage in the brain may result in muscle weakness, fatigue, unsteady gain, numbness, slurred speech, impaired vision, vertigo and the like.

Current therapies for multiple sclerosis include corticosteroid drugs (to alleviate the symptoms of acute episodes), as well as other biomolecules. In particular, beta-interferon (IFNβ) has been tested and approved by the U.S. Food and Drug Administration (FDA) as an MS therapy. Unfortunately, the presently-used therapies suffer from a range of problems. The drugs are often toxic at the doses required for a maximal therapeutic effect. Further, the body may become desensitized to the drug such that higher (and more toxic) doses are required to maintain even a minimal therapeutic effect.

The present invention provides a method of treatment for autoimmune diseases, such as MS, that does not have the toxic side effects associated with currently-used therapies.

SUMMARY OF THE INVENTION

In one embodiment, the present invention includes a method of treating multiple sclerosis in a subject in need of such treatment. The method includes administering, to the subject, a pharmaceutically effective amount of tau-interferon. The tau-interferon may be administered, for example, via intravenous or intramuscular injection. The tau interferon may be derived from (have an amino acid sequence corresponding to that of) a tau-interferon from any species that expresses tau-interferon protein (e.g., ovine, bovine, goat, ox, rat, mouse or human tau-interferon). The tau-interferon may be purified from a suitable source, produced recombinantly (i.e., recombinant tau-interferon), or produced synthetically. In addition, tau-interferon polypeptides (typically having between about 15 and 172 amino acids) can be used in the method of the present invention. The method of the invention may also include administering a second multiple sclerosis treatment agent a second treatment agent before, concurrently with, or after administering tau-interferon. Exemplary second agents include beta-interferon and corticosteroid drugs.

In a further embodiment, the present invention includes a method of treating lupus erythematosus in a subject in need of such treatment. The method includes administering, to the subject, a pharmaceutically effective amount of tau-interferon.

In another embodiment, the present invention includes a method of treating type I diabetes in a subject in need of such treatment. The method includes administering, to the subject, a pharmaceutically effective amount of tau-interferon.

In a further embodiment, the present invention includes a method of treating rheumatoid arthritis in a subject in need of such treatment. The method includes administering, to the subject, a pharmaceutically effective amount of tau-interferon.

The above-recited methods may also include administration by routes other than injection, for example, topical application or intraarterial infusion.

In a more general aspect, the present invention includes a method of treating an autoimmune disease in a subject in need of such treatment.

It is further contemplated that tau-interferon may be useful for treatment of either allograft or xenograft transplantation rejection.

These and other objects and features of the invention will become more fully apparent when the following detailed description is read in conjunction with the accompanying drawings.

DETAILED DESCRIPTION OF THE INVENTION

I. Definitions

Interferon-τ refers to any one of a family of interferon proteins having at least one characteristic from each of the following two groups of characteristics: (i) (a) anti-luteolytic properties, (b) anti-viral properties, (c) anti-cellular proliferation properties; and (ii) about 45 to 68% amino acid homology with α-Interferons and greater than 70% amino acid homology to known IFNτ sequences (e.g., Ott, et al., Helmer, et al., 1987, Imakawa, et al., 1989, Whaley, et al., 1994, Bazer, et al., 1994).

An interferon-τ polypeptide is a polypeptide having between about 15 and 172 amino acids derived from an interferon-τ amino acid coding sequence, where said 15 to 172 amino acids are contiguous in native interferon-τ. Such 15–172 amino acid regions can also be assembled into polypeptides where two or more such interferon-τ regions are joined that are normally discontinuous in the native protein.

Treating a disease refers to administering a therapeutic substance effective to reduce the symptoms of the disease and/or lessen the severity of the disease.

II. Overview of Invention

Experiments performed in support of the present invention indicate that IFNτ is effective at preventing the development of experimental allergic encephalomyelitis (EAE; Zamvil and Steinman, 1990), an animal model of antigen-induced autoimmunity that has been widely studied to gain insight into multiple sclerosis (MS). IFNτ is at least as effective in these experiments as IFNβ, which has recently been approved by the FDA for the treatment of MS. The experiments further show that IFNτ has a lower toxicity than IFNβ, and that IFNτ-treated mice do not develop leukopenia, an undesired side effect associated with IFNβ treatment.

It has recently been shown that superantigens can include relapses in EAE, similar to those that occur "spontaneously" in MS patients. Additional experiments performed in support of the present invention show that IFNτ blocks superantigen reactivation of EAE, and that the inhibitory effect of IFNτ on induction of EAE and reactivation by superantigen involves suppression of myelin basic protein (MBP) and superantigen activation of T cells as well as suppressed induction of destructive cytokines such as tumor necrosis factor. Taken together, these results indicate that IFNτ may be highly effective in treatment of autoimmune diseases, such as MS, with lower toxicity and fewer side effects than are associated with IFNβ.

III. Immune System Disorders

Diseases which may be treated using methods of the present invention include autoimmune, inflammatory, proliferative and hyperproliferative diseases, as well as cutaneous manifestations of immunologically mediated diseases. In particular, methods of the present invention are advantageous for treating conditions relating to immune system hypersensitivity. There are four types of immune system hypersensitivity (Clayman). Type I, or immediate/anaphylactic hypersensitivity, is due to mast cell degranulation in response to an allergen (e.g., pollen), and includes asthma, allergic rhinitis (hay fever), urticaria (hives), anaphylactic shock, and other illnesses of an allergic nature. Type II, or autoimmune hypersensitivity, is due to antibodies that are directed against perceived "antigens" on the body's own cells. Type III hypersensitivity is due to the formation of antigen/antibody immune complexes which lodge in various tissues and activate further immune responses, and is responsible for conditions such as serum sickness, allergic alveolitis, and the large swellings that sometimes form after booster vaccinations. Type IV hypersensitivity is due to the release of lymphokines from sensitized T-cells, which results in an inflammatory reaction. Examples include contact dermatitis, the rash of measles, and "allergic" reactions to certain drugs.

The mechanisms by which certain conditions may result in hypersensitivity in some individuals are generally not well understood, but may involve both genetic and extrinsic factors. For example, bacteria, viruses or drugs may play a role in triggering an autoimmune response in an individual who already has a genetic predisposition to the autoimmune disorder. It has been suggested that the incidence of some types of hypersensitivity may be correlated with others. For example, it has been proposed that individuals with certain common allergies are more susceptible to autoimmune disorders.

Autoimmune disorders may be loosely grouped into those primarily restricted to specific organs or tissues and those that affect the entire body. Examples of organ-specific disorders (with the organ affected) include multiple sclerosis (myelin coating on nerve processes), type I diabetes mellitus (pancreas), Hashimotos thyroiditis (thyroid gland), pernicious anemia (stomach), Addison's disease (adrenal glands), myasthenia gravis (acetylcholine receptors at neuromuscular junction), rheumatoid arthritis (joint lining), uveitis (eye), psoriasis (skin), Guillain-Barré Syndrome (nerve cells) and Grave's disease (thyroid). Systemic autoimmune diseases include systemic lupus erythematosus and dermatomyositis.

Other examples of hypersensitivity disorders include asthma, eczema, atopical dermatitis, contact dermatitis, other eczematous dermatitides, seborrheic dermatitis, rhinitis, Lichen planus, Pemplugus, bullous Pemphigoid, Epidermolysis bullosa, uritcaris, angioedemas, vasculitides, erythemas, cutaneous eosinophilias, Alopecia areata, atherosclerosis, primary biliary cirrhosis and nephrotic syndrome. Related diseases include intestinal inflammations, such as Coeliac disease, proctitis, eosinophilia gastroenteritis, mastocytosis, inflammatory bowel disease, Chrohn's disease and ulcerative colitis, as well as food-related allergies.

IV. Interferon-τ

The first IFNτ to be identified was ovine IFNτ (OvIFNτ). Several isoforms of the 18–19 kDa protein were identified in conceptus (the embryo and surrounding membranes) homogenates (Martal, et al., 1979). Subsequently, a low molecular weight protein released into conceptus culture medium was purified and shown to be both heat labile and susceptible to proteases (Godkin, et al., 1982). OvIFNτ was originally called ovine trophoblast protein-one (oTP-1) because it was the primary secretory protein initially produced by trophectoderm of the sheep conceptus during the critical period of maternal recognition in sheep. Subsequent experiments have determined that OvIFNτ is a pregnancy recognition hormone essential for establishment of the physiological response to pregnancy in ruminants, such as sheep and cows (Bazer and Johnson, 1991).

IFNτs with similar characteristics and activities have been isolated from other ruminant species including cows and goats (Bartol, et al., 1985; and Gnatek, et al., 1989). Antisera to all the IFNτs cross-react. This is not unexpected since the species specific forms of IFNτ are more closely homologous to each other than to the IFNsα from the identical species (Roberts, et al., 1992).

The cow protein (BoIFNτ; Helmer, et al., 1987; Imakawa, et al., 1989) has similar functions to OvIFNτ in maternal recognition of pregnancy. Further, it shares a high degree of amino acid and nucleotide sequence homology with OvIFNτ. The nucleic acid sequence homology between OvIFNτ and BoIFNτ is 76.3% for the 5' non-coding region, 89.7% for the coding region, and 91.9% for the 3' non-coding region. The amino acid sequence homology is 80.4%.

TABLE 1

OVERVIEW OF THE INTERFERONS

| Aspects | Type I | | | Type II |
|---|---|---|---|---|
| Types | α & ω | β | τ | γ |
| Produced by: | leukocyte | fibroblast | trophoblast | lymphocyte |
| Effects: | | | | |
| Antiviral | + | + | + | + |
| Antiproliferative | + | + | + | + |
| Pregnancy Signally | – | – | + | – |

While IFNτ displays many of the activities classically associated with type I IFNs (see Table 1, above), considerable differences exist between it and the other type I IFNs. The most prominent difference is its role in pregnancy, detailed above. Also different is viral induction. All type I IFNs, except IFNτ, are induced readily by virus and dsRNA (Roberts, et al., 1992). Induced IFNα and IFNβ expression is transient, lasting approximately a few hours. In contrast, IFNτ synthesis, once induced, is maintained over a period of days (Godkin, et al., 1982). On a per-cell basis, 300-fold more IFNτ is produced than other type I IFNs (Cross and Roberts, 1991).

Other differences may exist in the regulatory regions of the IFNτ gene. For example, transfection of the human trophoblast cell line JAR with the gene for bovine IFNτ resulted in antiviral activity while transfection with the bovine IFNΩ gene did not. This implies unique transacting factors involved in IFNτ gene expression. Consistent with this is the observation that while the proximal promoter region (from 126 to the transcriptional start site) of IFNτ is highly homologous to that of IFNα and IFNβ; the region from –126 to –450 is not homologous and enhances only IFNτ expression (Cross and Roberts, 1991). Thus, different regulatory factors appear to be involved in IFNτ expression as compared with the other type I IFNs.

IFNτ expression may also differ between species. For example, although IFNτ expression is restricted to a particular stage (primarily days 13–21) of conceptus development in ruminants (Godkin, et al., 1982), preliminary studies suggest that the human form of IFNτ is constitutively expressed throughout pregnancy (Whaley, et al., 1994).

A. Isolation of IFNτ

OvIFNτ protein may be isolated from conceptuses collected from pregnant sheep and cultured in vitro in a modified Minimum Essential Medium (MEM) as described by Godkin, et al., (1982) and Vallet, et al., (1987). The IFNτ may be purified from the conceptus cultures by ion exchange chromatography and gel filtration. The homogeneity of isolated IFNτ may be assessed by sodium dodecyl sulfate polyacrylamide gel electrophoresis (SDS-PAGE; Maniatis, et al.; Ausubel, et al.), and determination of protein concentration in purified IFNτ samples may be performed using the bicinchoninic (BCA) assay (Pierce Chemical Co., Rockford, Ill.; Smith, et al., 1985).

B. Recombinant Production of IFNτ

An IFNτ cDNA obtained by probing a sheep blastocyst library with a synthetic oligonucleotide representing the N-terminal amino acid sequence (Imakawa, et al., 1987) has a predicted amino acid sequence that is 45–55% homologous with IFNsα from human, mouse, rat and pig and 70% homologous with bovine IFNαII, now referred to as IFNΩ. Several cDNA sequences have been reported which may represent different isoforms (Stewart, et al., 1989a; Klemann, et al., 19990; and Charlier, M., et al., 1991). All are approximately 1 kb with a 585 base open reading frame that codes for a 23 amino acid leader sequence and a 172 amino acid mature protein. The predicted structure of IFNτ as a four helical bundle with the amino and carboxyl-termini in apposition further supports its classification as a type I IFN (Jarpe, et al., 1994).

The DNA encoding the IFNτ polypeptide can be cloned into any number of commercially available vectors to generate recombinant IFNτ in the appropriate host system. These systems include a number of bacterial expression vectors, such as lambda gt11 (Promega, Madison Wis.), pGEX (Smith, et al.), and pBS (Stratagene, La Jolla Calif.) vectors; yeast expression systems, such as the Pichia expression kit from Invitrogen (San Diego, Calif.); baculovirus expression systems (Reilly, et al.; Beames, et al.; Clontech, Palo Alto Calif.); and mammalian cell expression systems (Clontech, Palo Alto Calif.; Gibco-BRL, Gaithersburg Md.).

The plasmid pGEX (Smith, et al., 1988) and its derivatives (e.g., the pGEX series from Pharmacia Biotech, Piscataway, N.J.) express the polypeptide sequences of a cloned insert fused in-frame with glutathione-S-transferase. Recombinant pGEX plasmids can be transformed into appropriate strains of E. coli and fusion protein production can be induced by the addition of IPTG (isopropyl-thio galactopyranoside). Solubilized recombinant fusion protein can then be purified from cell lysates of the induced cultures using glutathione agarose affinity chromatography according to standard methods (Ausubel, et al.).

A number of features can be engineered into the expression vectors, such as leader sequences which promote the secretion of the expressed sequences into culture medium. The recombinantly produced polypeptides are typically isolated from lysed cells or culture media.

Recombinant protein can be purified by standard methods, including size fractionation (column chromatography or preoperative gel electrophoresis) or affinity chromatography (using, for example, anti-IFNτ antibodies (solid support available from Pharmacia, Piscataway N.J.). Protein preparations can also be concentrated by, for example, filtration (Amicon, Danvers, Mass.).

In addition to recombinant methods, IFNτ proteins or polypeptides can be isolated from selected cells by affinity-based methods, such as by using appropriate antibodies. Further, IFNτ peptides may be chemically synthesized using methods known to those skilled in the art.

C. IFNτ Lacks Toxicity

Type I IFNs (IFNα and IFNβ), as well as type II (IFNγ), exhibit significant cytotoxicity (Degre, 1974; Fent, et al., 1987). Detrimental toxic effects exerted by these IFNs have been observed during clinical trials and patient treatment, and include flu-like symptoms such as fever, chills and lethargy, tachycardia, nausea, weight loss, leukopenia, and neutropenia (Degre, 1974; Fent and Zbinden, 1987).

Experiments performed in support of the present invention and detailed in Example 1, below, suggest that IFNτ has significantly lower cytotoxicity than the IFNs listed above. Cytotoxicity was assessed in vivo (Example 1A) using white blood cell counts (WBC), lymphocytes percentages and total body weights of New Zealand White (NZW) mice injected with the various IFNs. The results are presented in Table 3 and summarized in Table 2. Twelve hours after injection with $10^5$ of murine interferon-alpha (MuIFNα), shown previously to induce a higher degree of toxicity than IFNβ, the mice exhibited decreased white blood cell counts, lymphopenia and substantial weight loss. None of these toxicity-related effects were observed in OvIFNτ-injected animals.

The concentrations of OvIFNτ used in the toxicity studies were the same as those shown to be effective at preventing EAE (detailed in Example 2, below).

Figure 1:
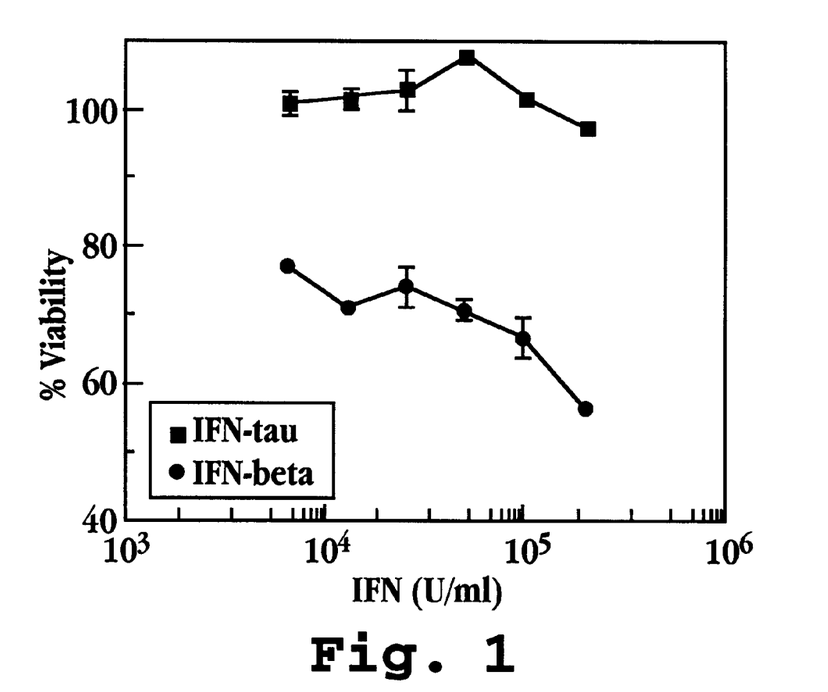
FIG. 1 shows a comparison of the toxicity of IFNβ and IFNτ.

Cytotoxicity was also assessed in vitro (Example 1B). Viability of L929 cells exposed IFNτ at concentrations as high as 200,000 U/ml remained near control levels, while IFNβ showed toxic effects at concentrations as low as 7,000 U/ml (FIG. 1). IFNτ was also found to lack toxicity when tested in a panel of tumorigenic cell lines, although it did inhibit cell replication.

Additional studies, comparing the toxicity of IFNτ with the toxicities of IFNβ and IFNα in animal models as well as tissue culture (Bazer and Johnson, 1991; Johnson, et al., 1994; Bazer, et al., 1989; and Soos and Johnson, 1995), are summarized in Table 2, below.

TABLE 2

PARAMETERS DEMONSTRATING THE LACK OF TOXICITY BY IFNτ BUT NOT IFNs α AND β

| | Toxicity | | |
|---|---|---|---|
| | IFNτ | IFNα | IFNβ |
| In vitro (cell viability) | | | |
| Mouse L929 (50,000–200,000 U/ml of IFN) | – | + | + |
| Bovine MDBK (50,000 U/ml of IFN) | – | + | ND |
| Human WISH (50,000 U/ml of IFN) | – | + | ND |
| Human Peripheral Lymphocytes (50,000 U/ml of IFN) | – | + | + |
| HIV Infected Human Peripheral Lymphocytes (50,000–500,000 U/ml of IFN | – | + | ND |
| In Vivo (NZW Mice) | | | |
| White Blood Cell Count | – | + | + |
| Lymphocyte Depression | – | + | + |
| Weight Measurement | – | + | ± |

Plus and minus signs indicate toxicity or lack thereof induced by treatment with the various type I IFNs. For in vivo studies, $10^5$ U were administered per injection and cell counts and weights were evaluated at either 12 or 24 hours after injection.
ND = not determined.

MDBK cells cultured in the presence of IFNs exhibited reduced viability when cultured in the presence of IFNα (50,000 U/ml), but not when cultured in the presence of IFNτ (Pontzer, et al., 1991). Similar results were obtained with the human WISH cell line. Comparisons of toxicity (or lack thereof) induced by IFNτ and other IFNs have been made using human peripheral mononuclear cells (HPMC) and HIV-infected HPMC. IFNτ did not exhibit toxic effects on cultured HPMC while both IFNα and IFNβ reduced cell viability at 50,000 U/ml (Soos and Johnson, 1995). Human lymphocytes infected with HIV-1 and feline lymphocytes infected with HIV also did not exhibit reduced viability in the presence of IFNτ (Bazer, et al., 1989). These findings indicate that the lack of toxicity of IFNτ inferred from observations using immortalized cell lines also applies to human peripheral blood.

The results summarized in Table 2 demonstrate that IFNτ appears to have little or no toxicity, when tested both in vitro and in vivo, as compared with IFNα, IFNβ and IFNτ.

V. IFNτ as a Treatment for Autoimmune Disorders

Compositions and methods of the present invention may be used to therapeutically treat and thereby alleviate a variety of immune system-related disorders characterized by hyper- or hypo-active immune system function. Such disorders include hyperallergenicity and autoimmune disorders, such as multiple sclerosis, type I (insulin dependent) diabetes mellitus, lupus erythematosus, amyotrophic lateral sclerosis, Crohn's disease, rheumatoid arthritis, stomatitis, asthma, allergies, psoriasis and the like.

A. IFNτ Treatment in EAE, an Animal Model for Multiple Sclerosis

1. OVIFNτ Inhibits Development of EAE, an Animal Model for Multiple Sclerosis.

The efficacy of IFNτ in treating autoimmune disorders may be evaluated in rodents with experimental allergic encephalomyelitis (EAE), an animal model of antigen-induced autoimmunity that is widely studied to gain insight into human multiple sclerosis (MS). EAE is an autoimmune demyelinating disease induced by immunizing susceptible mouse, rat or guinea pig strains with myelin basic protein (MBP) or with encephalitogenic peptide fragments. Genetic susceptibility in the model animal strains is based in part on the capacity of encephalitogenic peptides to bind to particular class II major histocompatibility complex (MHC-II) molecules (Fritz, et al., Wraith, et al.). In particular, mice having the H-2" haplotype are susceptible to EAE. Susceptible mouse strains include PL/J mice (Klein, et al.), (PL/J×SJL)F$_1$ mice (Zanvil, et al., Wraith, et al.), B10.PL mice (Figuero, et al.), NZW mice (Kotzin, et al.), and (NZB× NZW)F1 (Kotzin, et al.) mice.

Gamma-interferon (IFNγ) and beta-interferon (IFNβ) have been demonstrated to be effective in treating multiple sclerosis (Johnson, et al., 1994; IFNβ Multiple Sclerosis Study Group). In fact, IFNβ has been approved by the FDA as a therapeutic for multiple sclerosis. Although β-IFN is effective against MS, it has relatively high toxicity, and as a result, has a variety of undesirable side effects. As described above, however, IFNτ has significantly lower toxicity that other interferons and may therefore exhibit fewer undesirable side effects.

In experiments performed in support of the present invention and detailed in Example 2, IFN-τ was tested for its ability to prevent the induction of EAE. EAE was induced in New Zealand White (NZW) mice by immunization with bovine myelin basic protein (bMBP). The mice were injected intraperitoneally (i.p.) with either a single dose of recombinant ovine IFN-tau (OvIFNτ) or murine IFN-beta (MuIFN-β) on the day of, or 3 doses of OvIFN-τ or MuIFN-β 48 hours before, on the day of and 48 hours after immunization with MBP.

Figure 2:
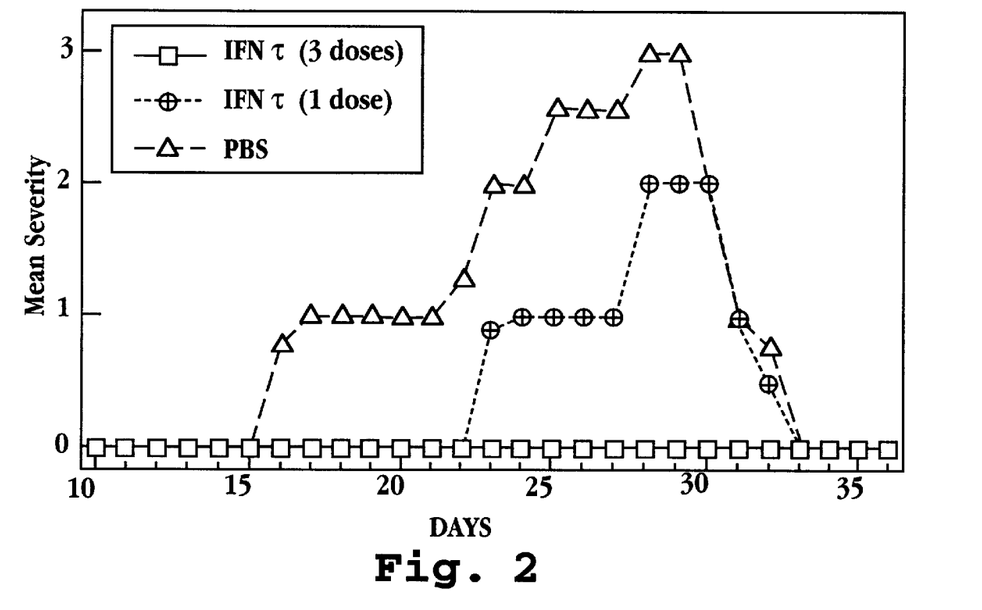
FIG. 2 shows the mean severity of experimental allergic encephalomyelitis (EAE) in New Zealand White (NZW) mice immunized with MBP in the presence and absence of IFNτ.

The results of the experiments are summarized in Table 4, below. A time course of the mean severity of EAE is presented in FIG. 2. Symbols are as follows: Δ—control animal; ⊕—single dose of OvIFNτ; □—3 doses of OvIFNτ.

All of the animals injected (both sham-injected and IFN-injected) on the day of the immunization developed EAE, but the severity was reduced, and the mean day of onset was delayed in both the OvIFNτ (23.8±0.5 days) and MuIFN-β (23.5±0.6 days) treated animals relative to control animals (16.2±0.8 days).

The results obtained using the 3-dose protocol are more striking. Seven of the nine control animals developed EAE an average of 15.2 days following immunization. In contrast, none of nine animals treated with OvIFNτ developed the disease, and one of nine animals treated with MuIFN-β succumbed to EAE (22 days after immunization).

The data demonstrate that IFNτ is an effective immunotherapy for the prevention of EAE, and is as effective a treatment in this model of autoimmune disease as MuIFNβ. Taken together with the lower toxicity of IFNτ relative to IFNβ, the data suggest that treatment of individuals having an autoimmune disorder (such as multiple sclerosis) with IFNτ may be preferable and more effective than treatment with IFNβ.

2. OvIFNτ Inhibits T-Cell Proliferation.

Figure 3:
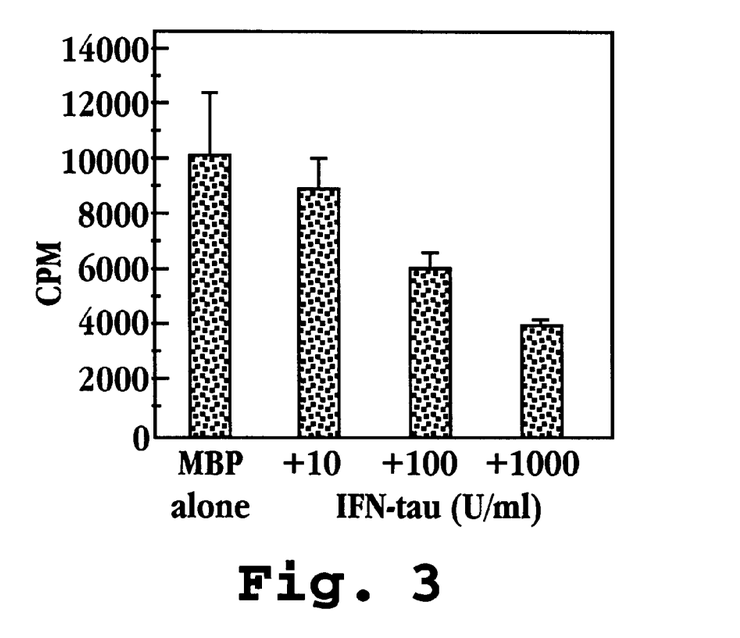
FIG. 3 shows the effects of IFNτ on proliferation of spleen cells from MBP-immunized NZW mice.

The effects of IFNτ on proliferation of spleen cells from MBP-immunized NZW mice stimulated with MBP in vitro were assessed. The results are shown in FIG. 3. Proliferation in response to MBP was vigorous and could be reduced by IFNτ in a dose-dependent manner, indicating that IFNτ has antiproliferative activity against T cells specific for the autoantigen, MBP. These results are consistent with the observation that IFNτ inhibits or eliminates symptoms of MBP-induced EAE, since inhibition of such T-cells would be expected to reduce the severity of the autoimmune response.

3. OvIFNτ Inhibits Superantigen Reactivation of EAE.

The symptomology of MS can often be observed to occur in a relapsing-remitting manner. This form of MS consists of presentation with clinical symptoms of MS followed by periods of remission. How relapses and exacerbations occur and what causes the reactivation of autoimmune disease has been a topic of much speculation. It has been suggested that environmental influences may contribute to or even be responsible for exacerbations of autoimmune disease. Such influences potentially include exposure to infectious agents as well as factors possessing immunostimulatory activity. One class of proteins which are ubiquitous in our environment are the microbial superantigens.

Microbial superantigens are toxins produced by a variety of bacteria, viruses, and other organisms such as mycoplasma that possess extremely potent immunostimulatory activity (Langford, et al., 1978; Carlsson, et al., 1985; and Johnson and Magazine, 1988). They are responsible for a number of maladies including food poisoning and toxic shock syndrome (Bergdoll, et al., 1981). Such powerful immunostimulation by superantigens is based on their ability to engage major histocompatibility complex class II molecules and then, as a binary complex, bind to the T cell receptor in a β-chain variable region (Vβ)-specific manner (Johnson, et al., 1991; Janeway, et al., 1989; White, et al., 1989; Carlsson, et al., 1988; and Fleischer and Schrezenmeier, 1988). This binding triggers T cell activation leading to proliferation of as much as 20% of a T cell repertoire (Johnson, et al., 1991).

Superantigen-induced T cell proliferation is accompanied by massive amounts of cytokine production including interleukin 2 (IL2), IFNγ, and tumor necrosis factor alpha (TNFα). Of the cytokines whose production is induced by superantigen stimulation, IFNγ and TNFα have been implicated as mediators of autoimmune pathogenesis. IFNγ has been shown to cause exacerbations of MS in clinical trials (Panitch, et al., 1987a; Panitch, et al., 1987b). Production of TNFα has been shown to be a requirement for the encephalitogenicity of certain T cell lines used to adoptively transfer EAE (Powell, et al., 1990) as well as causing myelin producing oligodendrocyte death in vitro (Selmaj and Raine, 1988).

Experiment performed in support of the present invention that Staphylococcus Enterotoxin B (SEB)-induced cytokine production is also altered by IFNτ. Spleen cells from MBP-immunized mice were stimulated with SEB in vitro in the presence or absence of IFNτ, and supernatants were examined for TNFα and IFNγ production. Addition of IFNτ to cultures stimulated with SEB significantly reduced production of both TNFα and IFNγ. In view of the above, these results are consistent with the ability of IFNτ to reduce the severity of EAE, and suggest that IFNτ may reduce exacerbations of MS.

Exacerbation evidenced as a clinical relapse of EAE was first demonstrated by the administration of a microbial superantigen. In the PL/J strain, acute episodes of EAE usually resolve and clinical relapses have been shown not to occur (Fritz, et al., 1983). After resolution of all clinical signs of EAE induced by immunization with MBP, administration of either of the Staphylococcus aureus enterotoxin (SE) superantigens, SEB or Staphylococcus Enterotoxin A (SEA), was shown to cause reactivation of disease (Schiffenbauer, et al., 1993). Multiple episodes of disease exacerbation over a four-month period were also shown in which EAE could be reactivated and resolved based on multiple injections of SEB (Schiffenbauer, et al., 1993). Reactivation of EAE by SEB has also been shown to occur in other susceptible strains including NZW. SEB can also reactivate disease when an acetylated amino terminal peptide of MBP is employed as the immunogen (Brocke, et al., 1993).

In addition to reactivation of EAE, SEB can also prevent EAE when administered prior to immunization with MBP (Soos, et al., 1993; and Kalman, et al., 1993). Anergy and/or deletion of the Vβ8$^+$ T cell subset which is responsible for the initial induction of EAE appears to be the mechanism for this protection. Targeting of a Vβ specific T cell population does not, however, provide absolute protection from development of EAE. When mice protected from development of EAE by SEB pre-treatment are exposed to SEA (which has a different Vβ T cell specificity from SEB), induction of EAE does occur. This SEA-induced EAE is characterized by severe paralysis and accelerated onset of clinical symptoms. Thus, the effects of microbial superantigens introduce a profound complexity to autoimmune disease models such as EAE, akin to the complexity of the pathogenesis observed in MS.

The effect of OvIFNτ treatment on exacerbations of EAE induced by superantigen is evaluated on NZW mice in Example 4. The studies have also been carried out on PL/J mice. Treatment with OvIFNτ when administered in 3 doses of $10^5$ U (48 hours prior to SEB injection, on the day of SEB injection and 48 hours after SEB injection) blocked EAE reactivation by superantigen. In comparison, untreated control groups exhibited superantigen reactivation of EAE consistent with previous studies (Schiffenbauer, et al., 1993).

The observation that OvIFNτ can block superantigen-induced exacerbations of EAE may be a corollary to the reduction in disease exacerbations in MS patients undergoing treatment with IFNβ1b. A summary of the studies showing that OvIFNτ can prevent development and superantigen reactivation of EAE is presented in Table 5. The results demonstrate that IFNτ can also modulate the effects of environmental factors on the course of autoimmune disease, such as MS.

Additional experiments performed in support of the present invention have further shown that a second immunization of MBP can not reactivate EAE, and that injection of superantigens can induce an initial episode of clinical disease in PL/J mice that had been immunized with MPB but did not develop EAE. The experiments further demonstrate that this induction can be blocked by treatment with IFNτ, and that IFNτ can block superantigen-induced exacerbations of EAE akin to the reduced exacerbations of disease observed in IFNβ1b treated MS patients.

4. IFNτ Inhibits Vβ-specific T-Cell Activation.

Figure 5:
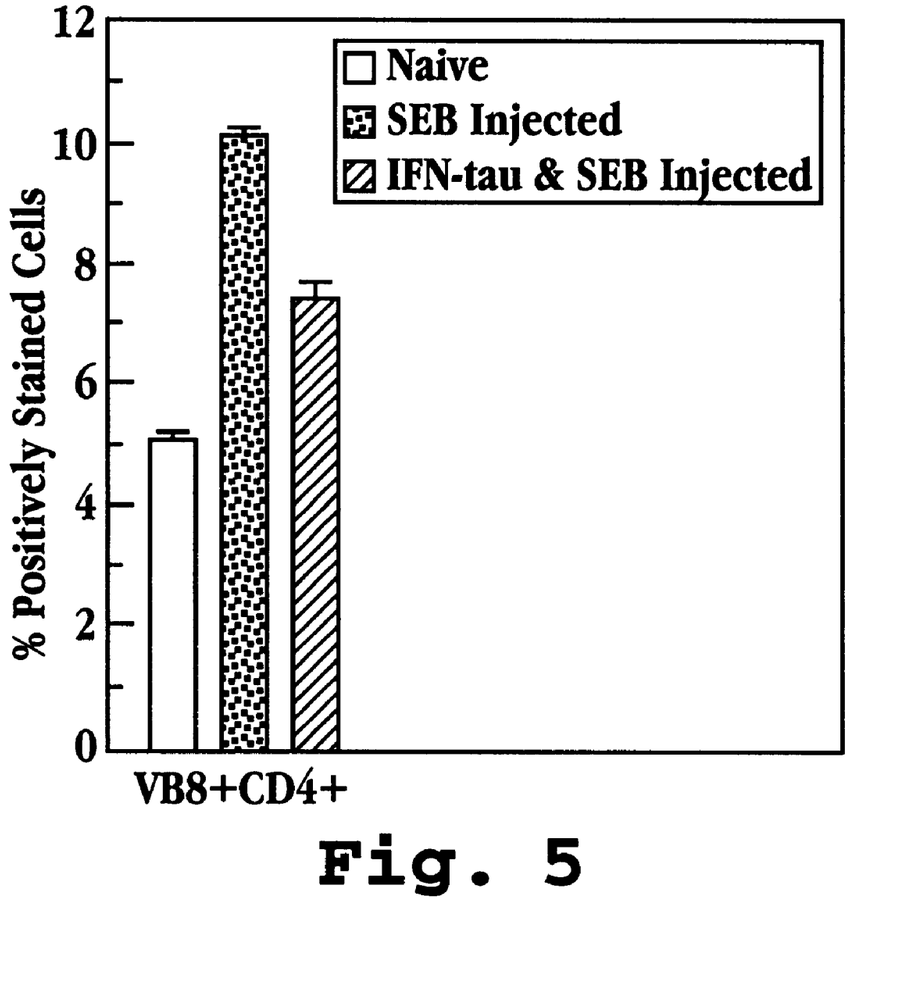
FIG. 5 shows the effects of IFNτ on Vβ-specific T-cell activation.

The effect of IFNτ treatment of SEB-induced Vβ specific T cell expansion in vitro was evaluated as described in Example 5. Vβ specific T-cell FACS analysis was performed on naive, SEB-injected, or IFNτ and SEB-injected NZW mice. Analyses were performed 72 hours after the injections.

Results of exemplary experiments are shown in FIG. 5. Open bars represent naive animals; closed bars represent SEB-injected animals, and crosshatched bars represent IFNτ- and SEB-injected animals. Naive NZW mice exhibited 5.1±0.1% Vβ8$^+$CD4$^+$ T cells, which was expanded to 10.2±0.2% after injection of SEB. When an IFNτ injection preceded the SEB injection, expansion of the Vβ8$^+$CD4$^+$ T-subset was limited to 7.6±0.2%. Partial inhibition of Vβ7$^+$ and Vβ11$^+$ T cells, for which SEB is also specific, was also observed.

These data indicate that treatment with IFNτ can partially inhibit SEB-induced Vβ T cell expansion in vivo, and further support the observation that IFNτ reduces the severity of MBP-induced EAE.

B. Other Autoimmune Disease Models

In addition to EAE, other animal models of autoimmune disease may be used to evaluate the therapeutic effects of IFNτ. For example, certain strains of mice are particularly susceptible to murine systemic lupus erythematosus, a disease analogous to systemic lupus erythematosus in humans. In particular, the MRL-lpr/lpr lupus mouse (Singer, et al.) exhibits many of the same immunological characteristics of human systemic lupus erythematosus. The animals have lymphoid organ enlargement and increased T-cell proliferation, with $V_\$$ gene expression significantly skewed in favor of $V_{\$8.2/8.3}$ genes (Singer, et al.).

MRL-lpr/lpr mice may be obtained from the Jackson Laboratory (Bar Harbor, Me.). The onset of disease in the MRL-lpr/lpr mice is spontaneous (at about 3 months of age), so the disease does not need to be induced as it does in the case of EAE. To evaluate the effects of IFNτ on the progression of disease, the animals are treated with injections of IFNτ (e.g., as described above) at selected intervals (e.g., once every two weeks) starting at a selected age (e.g., 6 weeks of age) for a selected duration (e.g., until 6 months of age).

The effects of the therapy may be evaluated in several ways. For example, the relative number of Vβ8$^+$ cells in spleens and lymph nodes of treated and untreated groups of animals may be determined using FACS analysis as described above. An effective dose of IFNτ results in a significant reduction of the number of Vβ8$^+$ T cells. Further, the physical symptoms of the disease (lymphoid hyperplasia, necrosis of ear, hair loss) may be quantitated (Kim, et al.) and compared between treated and untreated groups. The animals may also be assayed for the reduction of ds-DNA-specific antibody and/or reduction in nephritis with proteinuria, for example, as described in Kim, et al., following treatment with IFNτ.

Another animal model of an autoimmune disorder is adjuvant-induced arthritis in dogs (Kaplan, et al.).

VI. Administration of IFNτ

A. Pharmaceutical Compositions

Therapeutic preparations containing IFNτ or related polypeptides or proteins can be formulated according to known methods for preparing pharmaceutically useful compositions. Formulations comprising interferons or interferon-like compounds have been previously described (e.g., Martin, 1976). In general, the IFNτ therapeutic compositions will be formulated such that an effective amount of the IFNτ is combined with a suitable carrier and/or excipient in order to facilitate effective administration of the composition.

IFNτ, or related polypeptides, may be administered to a patient in any pharmaceutically acceptable dosage form, including intravenous, intramuscular, intralesional, or subcutaneous injection. Specifically, compositions and methods used for other interferon compounds can be used for the delivery of these compounds.

One primary advantage of IFNτ therapeutic compositions is the extremely low cytotoxicity of the IFNτ proteins. The IFNτ lack of toxicity and ability to ameliorate EAE indicate that IFNτ may be an effective immunotherapy for MS. Therapeutic effects exerted by IFNβ1b have been shown to be dose-dependent with higher dosages providing greater beneficial effects. Use of such higher dosages is limited, however, due to the toxic side effects of IFNβ1b. Because of the low cytotoxicity of IFNτ, it is possible to administer the IFNτ in concentrations which are greater than those which can generally be utilized for other interferon compounds (e.g., IFNα). Thus, IFNτ can be administered at rates from about $5 \times 10^4$ to $20 \times 10^6$ units/day to about $500 \times 10^6$ units/day or more. In a preferred embodiment, the dosage is about $10^6$ units/day. High doses are preferred for systemic administration.

It will, of course, be understood that the compositions and methods of this invention may be used in combination with other therapies. For example, in view of IFNτ's lack of toxicity at high dosages, MS patients that did not show improvement at IFNβ1b's low dosage or could not tolerate IFNβ1b due to toxicity may benefit from subsequent or simultaneous treatment with higher dosages of IFNτ or peptides derived therefrom. Further, development of neutralizing antibodies has been demonstrated in IFNβ1b treated patients (Weinstock-Guttman, et al., 1995). In cases where such neutralizing antibodies prove to impede the effectiveness of IFNβ1b, IFNτ may be an important alternative therapy, since antibody cross-reactivity is unlikely to occur.

Once improvement of a patient's condition has occurred, a maintenance dose is administered if necessary. Subsequently, the dosage or the frequency of administration, or both, may be reduced, as a function of the symptoms, to a level at which the improved condition is retained. When the symptoms have been alleviated to the desired level, treatment may cease. Patients may, however, require intermittent treatment on a long-term basis upon any recurrence of disease symptoms.

Autoimmune disorders effecting the skin, such as psoriasis, can be treated intralesionally using IFNτ, wherein formulation and dose will depend on the method of administration and on the size and severity of the lesion to be treated. Preferred methods include intradermal and subcutaneous injection. Multiple injections into large lesions may be possible, and several lesions on the skin of a single patient may be treated at one time. The schedule for administration can be determined by a person skilled in the art. Formulations designed for sustained release can reduce the frequency of administration.

Regional treatment with the IFNτ polypeptides of the present invention is useful for treatment of autoimmune diseases in specific organs. Treatment can be accomplished by intraarterial infusion or intravenous injection. A catheter can be surgically or angiographically implanted to direct treatment to the affected organ. A subcutaneous portal, connected to the catheter, can be used for chronic treatment, or an implantable, refillable pump may also be employed.

Alternatively, the composition may be administered by direct injection into the affected tissue. For treating rheumatoid arthritis, for example, the composition may be administered by direct injection into the affected joint. The patient may be treated at repeated intervals of at least 24 hours, over a several week period following the onset of symptoms of the disease in the patient.

Systemic treatment is essentially equivalent for all applications. Multiple intravenous or subcutaneous doses are possible, and in the case of implantable methods for treatment, formulations designed for sustained release are particularly useful. Patients may also be treated using implantable subcutaneous portals, reservoirs, or pumps. Other methods of administration include oral and suppository. For the treatment of systemic lupus erythematosus (SLE) or MS, for example, the composition may be administered by oral or parenteral administration, such as IV administration.

The compositions used in these therapies may also be in a variety of forms. These include, for example, solid, semi-solid, and liquid dosage forms, such as tablets, pills, powders, liquid solutions or suspensions, and liposomes. The preferred form depends on the intended mode of administration and therapeutic application.

VII. Veterinary Applications

In addition to the uses of the methods of the present invention detailed above, it will be appreciated that the methods may be applied to the treatment of a variety of immune system disorders suffered by domesticated and wild animals. For example, hypothyroidism in dogs typically results from a progressive destruction of the thyroid, which may be associated with Lymphocytic thyroiditis (Kemppainen and Clark). Lymphocytic thyroiditis, which resembles Hashimoto's thyroiditis in humans, is thought to be an autoimmune disorder. According to the guidance presented herein, hypothyroidism due to Lymphocytic thyroiditis in dogs may be treated with IFNτ, for example, as described above.

Another type of autoimmune disorder in dogs that may be alleviated by treatment with IFNτ is characterized by anti-nuclear antibody (ANA) positivity, pyrexia and seronegative arthritis (Day, et al.). Immune-mediated thrombocytopenia (ITP; Kristensen, et al.; Werner, et al.), systemic lupus erythematosus (Kristensen, et al.), and leukopenia and Coomb's positive hemolytic anemia (Werner, et al.), may also be amenable to treatment using methods of the present invention.

The following examples illustrate but in no way are intended to limit the present invention.

MATERIALS AND METHODS

A. Buffers

Phosphate-buffered saline (PBS)

10× stock solution, 1 liter:
  80 g NaCl
  2 g KCl
  11.5 g $Na_2HPO_4$—$7H_2O$
  2 g $KH_2PO_4$ Working solution, pH 7.3:
  137 mM NaCl
  2.7 mM KCl
  4.3 mM $Na_2HPO_4$—$7H_2O$
  1.4 mM $KH_2PO_4$

EXAMPLE 1

Toxicity of IFNβ, IFNγ and IFNτ

A. In Vivo Toxicity—Cell Counts and Weight Changes

The effects of in vivo treatment with IFNτ, IFNβ and IFNα ($10^5$ U/injection) on total white blood cell (WBC), total lymphocyte counts and weight measurements in NZW mice were assessed as follows. Interferons (OvIFNτ, MuIFNβ, and MuIFNα) were injected intraperitoneally (i.p.) at a concentration of $10^5$ U in a total volume of 0.2 ml in PBS into groups of New Zealand White (NZW) mice (Jackson Laboratories, Bar Harbor, Me.). Three to four animals were included in each group. White blood cell (WBC) counts were determined before injection and at selected timepoints thereafter (typically 12 and 24 hours) using a hemocytometer and standard techniques. Differential WBC counts were performed on Wright-Giemsa stained blood smears. Before injection, the weights of the animals ranged from 20 to 23 grams.

The results are summarized in Table 3, below.

TABLE 3

IN VIVO TOXICITY OF INTERFERONS AS MEASURED
BY WHITE BLOOD CELL COUNTS AND PERCENT WEIGHT CHANGE

| | Cell Count (Cell No. × $10^3$) | | | | % Lymphocyte Depression | % Weight Change 24 Hours after Injection |
|---|---|---|---|---|---|---|
| | Before Injection | | 12 hr. after Injection | | | |
| IFN | Total WBC | Lymphocytes | Total WBC | Lymphocytes | | |
| none | 7.3 ± 1.0 | 6.4 ± 0.7 | 8.0 ± 0.8 | 7.1 ± 0.7 | 0 | +0.5 ± 0.7 |
| τ | 6.7 ± 0.7 | 5.9 ± 0.6 | 6.7 ± 0.5 | 5.8 ± 0.4 | 1.7 | +1.3 ± 0.5 |
| β | 7.0 ± 1.4 | 6.0 ± 0.5 | 6.8 ± 0.8 | 4.1 ± 0.3 | 31.7 | −20.0 ± 1.0 |
| α | 6.0 ± 0.8 | 5.2 ± 0.7 | 4.8 ± 0.5 | 2.3 ± 0.2 | 55.8 | −8.5 ± 2.0 |

No significant differences in WBC counts, lymphocyte counts or weight change were observed between IFNτ-treated and untreated mice. In contrast, IFNβ-treated mice exhibited a 31.7% depression in lymphocyte counts 12 hours after injection, which continued for at least the next 12 hours. IFNα-treated mice exhibited a 55.8% lymphocyte depression and significant weight loss 12 hours after injection. These data indicate that, unlike IFNβ and IFNα, IFNτ lacks toxicity in vivo at the above concentrations as evidenced by peripheral blood cell counts and weight measurements.

B. In Vitro Toxicity—L929 Cell Assay

The toxicity of IFN treatment was measured in vitro using the mouse L929 cell line. L929 cells were treated with 6000 U/ml to 200,000 U/ml of either OvIFNτ or MuIFNβ. The interferons were added at time zero and the cells were incubated for 72 hours and stained with crystal violet. The percentage of living cells was determined by measuring the absorbance at 405 nm.

Exemplary data are shown in FIG. 1. Values are presented as percent viability ± standard error in which 100 percent is equal to the viability of L929 cells treated with media alone. At 6000 U/ml, IFNβ-treated cells exhibited a 77.0±0.6% viability. Viability of L929 cells decreased as the concentrations of IFNβ increased in a dose-dependent manner. In contrast, L929 cells showed no decrease in viability at any of the IFNτ concentrations tested. These data indicate that, unlike IFNβ, IFNτ lacks toxicity at high concentrations in vitro.

Taken together, the results summarized above demonstrate that IFNτ is essentially non-toxic at concentrations at which IFNβ induces toxicity both in vitro and in vivo.

EXAMPLE 2

IFNτ Inhibits Development of Experimental Allergic Encephalomyelitis

IFN-τ was tested for its ability to prevent the induction of EAE. Recipient NZW mice were injected i.p. with either a single dose of $10^5$ U/ml recombinant ovine IFN-tau (OvIFNτ) or murine IFN-beta (MuIFN-β; Lee Biomolecular, San Diego, Calif.) on the day of immunization with bovine myelin basic protein (bMBP) for induction of EAE or 3 doses of $10^5$ U/ml of OvIFN-τ or MuIFN-β 48 hours before, on the day of and 48 hours after immunization with MBP for induction of EAE.

Recombinant OvIFNτ was expressed in *Pichia pastoris* using a synthetic gene construct. The protein was secreted into the medium and purified by successive DEAE-cellulose and hydroxyapatite chromatography to electrophoretic homogeneity as determined by SDS-PAGE and silver staining. The purified protein had a specific activity of 0.29 to $0.44 \times 10^8$ U/mg.

For induction of EAE, 300 μg of bMBP was emulsified in complete Freund's adjuvant containing 8 mg/ml of H37Ra and injected on either side of the base of the tail. On the day of immunization and 48 hours later, 400 ng of Pertussis toxin (List Biologicals, Campbell, Calif.) was also injected. Mice were examined daily for signs of EAE and severity of disease was graded on the following scale: 1, loss of tail tone; 2, hind limb weakness; 3, paraparesis; 4, paraplegia; 5, moribund/death.

TABLE 4

Effects of IFN-τ on Development of EAE

| Treatment | # of IFN Doses | Disease Incidence | Mean Day of Onset | Mean Severity |
|---|---|---|---|---|
| none | 0 | 5/5 | 16.2 ± 0.8 | 3.0 ± 1.0 |
| oIFNτ | 1 | 5/5 | 23.8 ± 0.5 | 2.0 ± 1.0 |
| MuIFN-β | 1 | 4/4 | 23.5 ± 0.6 | 2.1 ± 1.6 |
| None | 0 | 7/9 | 15.3 ± 1.4 | 2.6 ± 0.8 |
| oIFNτ | 3 | 0/9 | — | — |
| MuIFN-β | 3 | 1/9 | 22 | 0.5 |

The results of the experiments are summarized in Table 4, above. The data are split into two sets. The first set (first three rows) corresponds to experiments where IFN was injected into experimental animals on the day of the immunization. All of the animals in this set developed EAE, but the mean day of onset was delayed in both the OvIFNτ (23.8±0.5 days) and MuIFN-β (23.5±0.6 days) treated animals relative to control animals (16.2±0.8 days). Further, the mean severity of the disease, quantitated as described above, was reduced in both IFN-treated groups relative to controls.

Like OvIFNτ, a single dose of $10^5$ U of MuIFNβ also caused a 7 day delay in the development of disease.

The results are more striking for the multiple dose protocol (rows 4–6 of Table 1), where three doses of IFN (48 hours prior, day of, and 48 hours post immunization) were administered to the experimental animals. Although seven of the nine control animals developed EAE an average of 15.2 days following immunization, none of nine animals treated with OvIFNτ developed the disease. Of the nine animals treated with MuIFN-β, one succumbed to EAE 22 days after immunization.

A time course of the mean severity from the experiments described above is presented in FIG. 2. Data from control animals are indicated by (Δ), data from animals treated with a single dose of OvIFNτ are indicated by (⊕), and data from animals that received 3 doses of OvIFNτ are indicated by (□).

The data demonstrate that IFNτ is an effective immunotherapy for the prevention of EAE and is as effective a treatment as MuIFNβ in this model of autoimmune disease. Taken together with the lower toxicity of IFNτ relative to IFNβ, the data suggest that treatment of individuals having an autoimmune disorder (such as multiple sclerosis) with IFNτ may be preferable and more effective than treatment with IFNβ.

EXAMPLE 3

IFNτ Inhibition of T-Cell Proliferation

The effects of IFNτ on proliferation of spleen cells from MBP-immunized NZW mice stimulated with MBP in vitro were determined as follows. Spleen cells from NZW mice immunized with bMBP were cultured in 300 μg/ml of bMBP in the presence of [$^3$H]thymidine and 0, 10, 100, or 1000 U/ml of OvIFNτ. Proliferation was measured by [$^3$H] thymidine incorporation.

The results are shown in FIG. 3. Data are presented as mean counts per minute (cpm) of triplicate samples. Background cpm have been subtracted from the cpm values presented. Proliferation in response to MBP was vigorous and could be reduced by IFNτ in a dose-dependent manner. 1000 U/ml IFNτ reduced proliferation to less than half of that observed in response to MBP alone.

These results demonstrate that IFNτ has antiproliferative activity against T cells specific for the autoantigen, MBP, and are consistent with the observation that IFNτ inhibits or eliminates symptoms of MBP-induced EAE.

EXAMPLE 4

IFNτ Prevents Superantigen Reactivation

IFNτ was examined for its ability to prevent superantigen reactivation of EAE in NZW mice (Jackson Laboratory, Bar Harbor, Me.). Schematic diagrams of the protocol followed in these experiments are shown in FIGS. 4A, 4B, 4C, 4D, 4E and 4F. These figures are referred to in the context of the protocol described below.

Figure 4A:
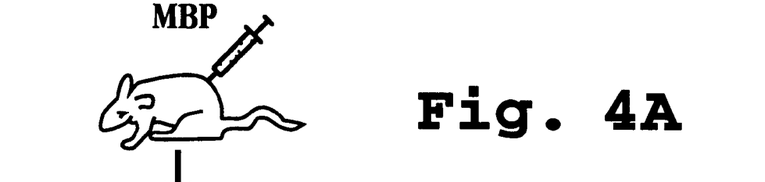
FIGS. 4A, 4B, 4C, 4D, 4E and 4F are graphic depictions of superantigen reactivation of EAE in the presence and absence of IFNτ.
Figure 4B:
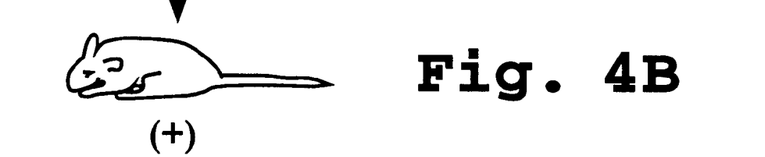
Figure 4C:
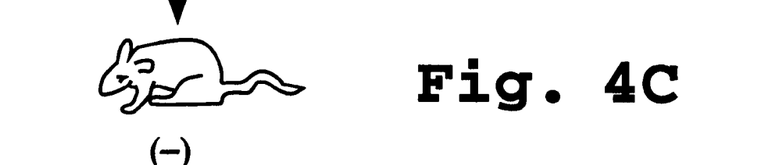

For induction of EAE, 300 μg of bMBP and 400 ng of Pertussis toxin (List Biological Technologies, Campbell, Calif.) were emulsified in complete Freund's adjuvant containing 8 mg/ml of H37Re and injected on either side of the base of the tail (FIG. 4A). Another injection containing 400 ng of Pertussis toxin was administered 48 hours later. The injections induced EAE, which peaked (FIG. 4B) and gradually tapered off, such that eventually, all clinical symptoms of EAE were resolved (FIG. 4C).

Figure 4D:
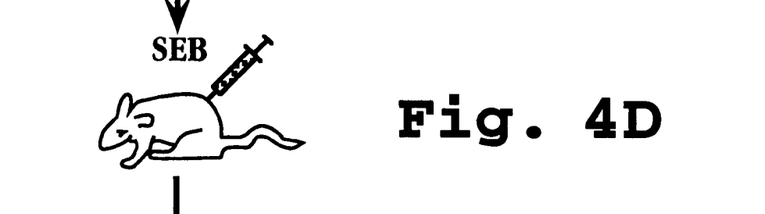
Figure 4E:
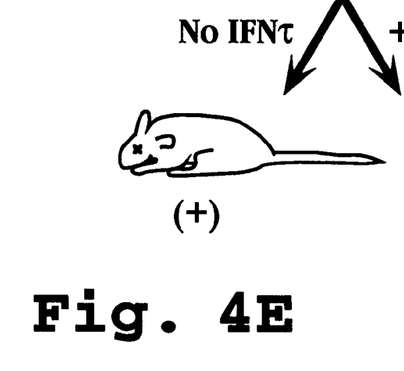
Figure 4F:
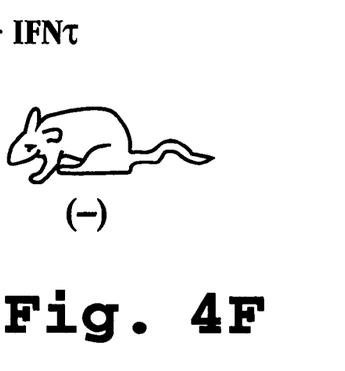

SEB was administered one month after resolution of disease (FIG. 4D). The mice were injected i.p. with 3 doses of $10^5$ U of IFNτ 48 hours before, on the day of, and 48 hours after injection of 40 μg SEB (Toxin Technology, Sarasota, Fla.) and 400 ng of Pertussis toxin (List Biological Technologies, Campbell, Calif.) (in 0.2 ml PBS) for superantigen reactivation. Control mice received SEB and Pertussis toxin only. The IFNτ preparation was identical to that described in Example 2. Mice were examined daily for signs of EAE and severity of disease was graded on the following scale: 1, loss of tail tone; 2, hind limb weakness; 3, paraparesis; 4, paraplegia; 5, moribund/death.

TABLE 5

IFNτ PREVENTS SUPERANTIGEN REACTIVATION OF EAE

| Treatment | No. of IFN Doses | Disease Incidence | Mean Day of Onset | Mean Severity |
| --- | --- | --- | --- | --- |
| Expt. 1 | | | | |
| none | 0 | 3/4 | 6.0 ± 1.7 | 1.6 ± 0.5 |
| OvIFNτ | 3 | 0/4 | — | — |
| Expt. 2 | | | | |
| none | 0 | 3/5 | 10.0 ± 2.5 | 1.4 ± 0.4 |
| OvIFNτ | 3 | 0/5 | — | — |

The data are summarized in Table 5, above. Of a total of nine control mice (receiving no IFNτ), six developed a reactivation of EAE. The mean day of onset was 6±1.7 in the first experiment, and 10±2.5 in the second experiment. Mean severity of the disease was 1.6±0.5 in the first experiment, and 1.4±0.4 in the second experiment. Of the nine animals that were treated with IFNτ, however, none developed symptoms of the disease.

EXAMPLE 5

IFNτ Inhibits Vβ-specific T-Cell Activation

The effect of IFNτ treatment of SEB-induced Vβ specific T cell expansion in vitro was evaluated as follows. All FACS reagents were obtained from Pharmingen (San Diego, Calif.).

Vβ specific T-cell FACS analysis was performed on naive, SEB-injected (50 μg) or IFNτ ($10^5$ U) and SEB (50 μg) injected NZW mice. All injections were i.p. and were administered as described in Example 3. Analyses were performed 72 hours after the injections.

For FACS analysis, ~$10^6$ T cells were isolated from the animals and incubated with biotin-labeled anti-Vβ antibodies for 45 minutes. The cells were then washed and incubated with strepavidin-phycoerythrin for 15 minutes, followed by another wash and a 45 minute incubation with FITC-labeled anti-CD4 antibodies. The cells were washed again and analyzed on a FACSort (Becton-Dickinson, Mountain View, Calif.) in duplicate as 10,000 events per sample.

Results of exemplary experiments are shown in FIG. 5. Open bars represent naive animals; closed bars represent SEB-injected animals, and crosshatched bars represent IFNτ- and SEB-injected animals. Values are presented as percentage of positively stained cells ± standard error. Values for the Vβ8$^+$CD4$^+$ T cell subset of SEB-injected and IFNτ- and SEB-injected were significantly different as shown by student's t test (P<0.02). Naive NZW mice exhibited 5.1±0.1% Vβ8$^+$CD4$^+$ T cells. After injection with 50 μg of SEB, this subset was expanded to 10.2±0.2%. When $10^5$ U of IFNτ preceded SEB injection, expansion of the Vβ8$^+$CD4$^+$ T-subset was limited to 7.6±0.2%. Partial inhibition of Vβ7$^+$ and Vβ11$^+$ T cells, for which SEB is also specific, was also observed.

These data indicate that treatment with IFNτ can partially inhibit SEB-induced Vβ T cell expansion in vivo, and further support the observation that IFNτ inhibits or eliminates symptoms of MBP-induced EAE.

While the invention has been described with reference to specific methods and embodiments, it is appreciated that various modifications and changes may be made without departing from the invention.

It is claimed:

1. A method of treating multiple sclerosis in a subject in need of such treatment, comprising administering to said subject a pharmaceutically effective amount of tau-interferon.

2. The method of claim 1, wherein said administering is injection.

3. The method of claim 1, wherein said tau-interferon is ovine tau-interferon.

4. The method of claim 1, wherein said tau-interferon is human tau-interferon.

5. The method of claim 1, wherein said tau-interferon is a recombinantly produced tau-interferon.

6. The method of claim 1, where said administering further includes administrating a second multiple sclerosis treatment agent.

7. The method of claim 6, where said administering of a second treatment agent is before or after administering tau-interferon.

8. The method of claim 6, where said administering of a second treatment agent is coincident with administering tau-interferon.

9. The method of claim 6, where said second agent is beta interferon.

10. The method of claim 6, where said second agent is a corticosteroid drug.

11. The method of claim 1, wherein said administering is by oral delivery.

* * * * *